(12) United States Patent
Nett et al.

(10) Patent No.: US 8,188,295 B2
(45) Date of Patent: May 29, 2012

(54) METHOD FOR PRODUCING DIFLUOROMETHYL-SUBSTITUTED PYRAZOLE COMPOUNDS

(75) Inventors: Markus Nett, Schifferstadt (DE);
Thomas Grote, Wachenheim (DE); Jan Klaas Lohmann, Ludwigshafen (DE);
Jochen Dietz, Mannheim (DE);
Sebastian Peer Smidt, Mannheim (DE);
Michael Rack, Eppelheim (DE);
Thomas Zierke, Boehl-Iggelheim (DE)

(73) Assignee: BASF SE, Ludwigshafen (DE)

( * ) Notice: Subject to any disclaimer, the term of this patent is extended or adjusted under 35 U.S.C. 154(b) by 253 days.

(21) Appl. No.: 12/664,448

(22) PCT Filed: Jun. 13, 2008

(86) PCT No.: PCT/EP2008/057506
§ 371 (c)(1),
(2), (4) Date: Dec. 14, 2009

(87) PCT Pub. No.: WO2008/152138
PCT Pub. Date: Dec. 18, 2008

(65) Prior Publication Data
US 2010/0184994 A1 Jul. 22, 2010

(30) Foreign Application Priority Data
Jun. 15, 2007 (EP) .................................... 07110397

(51) Int. Cl.
*C07D 231/14* (2006.01)
*C07C 229/06* (2006.01)
(52) U.S. Cl. ..................................... 548/374.1; 560/170
(58) Field of Classification Search .................. None
See application file for complete search history.

(56) References Cited

U.S. PATENT DOCUMENTS

| 5,093,347 | A | 3/1992 | Graneto et al. |
|---|---|---|---|
| 2006/0262944 | A1 | 11/2006 | Rassmussen et al. |
| 2006/0276656 | A1 | 12/2006 | Lantzsch et al. |
| 2008/0015244 | A1 | 1/2008 | Dunkel et al. |
| 2010/0022782 | A1 | 1/2010 | Zierke et al. |
| 2010/0174094 | A1 | 7/2010 | Kierke et al. |

FOREIGN PATENT DOCUMENTS

| DE | 39 34 924 | 4/1991 |
|---|---|---|
| DE | 103 31 496 | 1/2005 |
| JP | 59046273 | 3/1984 |
| WO | WO 92/12970 | 8/1992 |
| WO | WO 93/11117 | 6/1993 |
| WO | WO 03/070705 | 8/2003 |
| WO | WO 2005/042468 | 5/2005 |
| WO | WO 2005/044804 | 5/2005 |
| WO | WO 2007/031323 | 3/2007 |
| WO | WO 2007/051981 | 5/2007 |
| WO | WO 2008/022777 | 2/2008 |
| WO | WO 2008/053043 | 5/2008 |
| WO | WO 2008/077907 | 7/2008 |
| WO | WO 2008/145740 | 12/2008 |

OTHER PUBLICATIONS

Brough, P.A., et al., "3-(5-chloro-2,4-dihydroxyphenyl)-Pyrazole-4-carboxamides as inhibitors of the Hsp90 molecular chaperone", Bioorganic & Medicinal Chemistry Letters, 2005, p. 5197-5201, vol. 15.

(Continued)

*Primary Examiner* — Kamal Saeed
(74) *Attorney, Agent, or Firm* — Brinks Hofer Gilson & Lione

(57) ABSTRACT

The present invention relates to a process for preparing 3-difluoromethyl-Substituted pyrazole compounds of the formula (I)

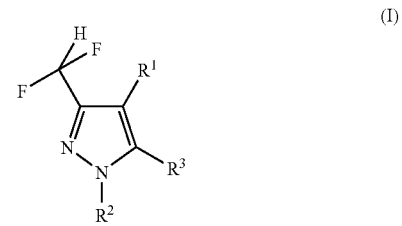

(I)

in which $R^1$ is H, halogen, nitro, $C_1$-$C_8$-alkyl, $C_1$-$C_8$-haloalkyl, $C_3$-$C_8$-cycloalkyl, phenyl, naphthyl, hetaryl, cyano, —C(=O)—$OR^{1a}$, —C(=O)—$NR^{1b}R^{1c}$, —C(=O)—$SR^{1d}$ or —C(=S)—$SR^{1e}$; $R^2$ is H, $C_1$-$C_4$-alkyl, benzyl or phenyl; $R^3$ is H, halogen, $C_1$-$C_8$-alkoxy, $C_1$-$C_8$-haloalkoxy, $C_3$-$C_8$-cycloalkoxy, $C_2$-$C_8$-alkenyloxy, $C_1$-$C_8$-alkylthio, $C_1$-$C_8$-haloalkylthio, $C_3$-$C_8$-cyclo-alkylthio or $C_2$-$C_8$-alkenylthio; compounds of the formula (II.a) or (II.b),

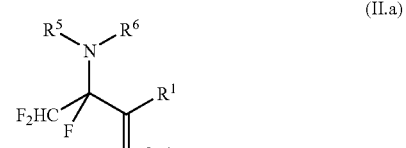

(II.a)

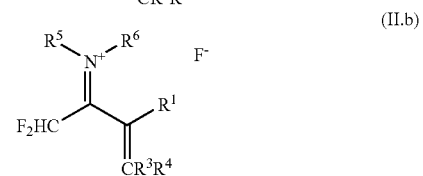

(II.b)

in which $R^1$ and $R^3$ each have one of the definitions given above; $R^4$ is halogen, —$OR^{4a}$, —$SR^{4a}$, —O—$SO_2$—$R^{4a}$ or an —$NR^{4b}R^{4c}$ group; $R^5$ and $R^6$ are each $C_1$-$C_8$-alkyl, $C_1$-$C_8$-haloalkyl, $C_3$-$C_8$-cycloalkyl, benzyl or phenyl, or, together with the nitrogen atom to which they are bonded, are a 3- to 8-membered heterocycle; Lewis acid adducts of compounds of the formula (II.b); the use of compounds of the formula (II.a) or (II.b) and of the Lewis acid adducts for preparing compounds of the formula (I) or (VI);
and to a process for converting such compounds to the corresponding 3-difluoro-pyrazol-4-ylcarboxylic acids.

12 Claims, No Drawings

OTHER PUBLICATIONS

Huang, Z., "Studies on the Synthesis of 3-substituted and 1,3 disubstituted pyrazoles via condensation of beta-chlorobinyl ketones with hydrazides", Gaodeng Xuexiao Huaxue Xuebao, 1992, p. 367-373, vol. 3, No. 3.

International Preliminary Report on Patentability dated Aug. 25, 2009, from corresponding International Application No. PCT/EP2008/057506, filed Jun. 13, 2008.

International Search Report completed Mar. 31, 2009, in International Application No. PCT/EP2008/057506, filed Jun. 13, 2008.

Gupton, John T. et al., "The application of vinylogous iminium salt derivatives to the regiocontrolled preparation of heterocyclic appended pyrazoles", Tetrahedron, 2002, p. 5467-5474, vol. 58.

Merceron, Nathalie, et al., "C-Phosphanyl-C-chloroiminium salts as electrophilic carbene synthetic equivalents", Chemical Communications, 2002, p. 2250-2251.

Petrov, Viacheslav A. et al., "1,1,2,2-Tetrafluoroethyl-N,N-dimethylamine: a new selective fluorinating agent", Journal of Fluorine Chemistry, 2001, p. 25-31, vol. 109.

METHOD FOR PRODUCING DIFLUOROMETHYL-SUBSTITUTED PYRAZOLE COMPOUNDS

This application is a National Stage application of International Application No. PCT/EP2008/057506 filed Jun. 13, 2008, the entire contents of which is hereby incorporated herein by reference. This application also claims the benefit under 35 U.S.C. §119 of European Patent Application No. 07110397.2 filed Jun. 15, 2007, the entire contents of which is hereby incorporated herein by reference.

DESCRIPTION

The present invention relates to a process for preparing 3-difluoromethyl-substituted pyrazole compounds of the formula (I)

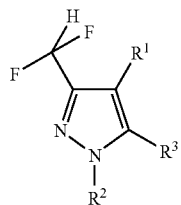

(I)

in which
$R^1$ is hydrogen, halogen, nitro, $C_1$-$C_8$-alkyl, $C_1$-$C_8$-haloalkyl, $C_3$-$C_8$-cycloalkyl, phenyl, naphthyl, hetaryl, cyano, —C(=O)—OR$^{1a}$, —C(=O)—NR$^{1b}$R$^{1c}$, —C(=O)—SR$^{1d}$ or —C(=S)—SR$^{1e}$, where the phenyl, naphthyl and hetaryl groups are each unsubstituted or have 1, 2 or 3 substituents selected independently from halogen, CN, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, —C(=O)—OR$^{1f}$, —C(=O)—NR$^{1g}$R$^{1h}$, S(=O)—R$^{1i}$ or S(=O)$_2$—R$^{1j}$, where $R^{1a}$, $R^{1d}$, $R^{1e}$, $R^{1f}$ are each independently $C_1$-$C_8$-alkyl, $C_1$-$C_8$-haloalkyl, $C_3$-$C_8$-cycloalkyl, $C_1$-$C_4$-alkoxy-$C_1$-$C_4$-alkyl, $C_3$-$C_8$-cycloalkoxy-$C_1$-$C_4$-alkyl, $C_2$-$C_8$-alkenyl, benzyl or phenyl, where the phenyl group in benzyl and phenyl is in each case unsubstituted or has 1, 2 or 3 substituents selected independently from halogen, CN, nitro, $C_1$-$C_4$-alkyl, $C_1$-$C_4$-haloalkyl, $C_1$-$C_4$-alkoxy and $C_1$-$C_4$-haloalkoxy, $R^{1b}$ is hydrogen, $C_1$-$C_8$-alkyl, $C_1$-$C_8$-haloalkyl, $C_3$-$C_8$-cycloalkyl, benzyl, phenyl or biphenylyl, where the phenyl groups in benzyl, phenyl and biphenylyl are each unsubstituted or have 1, 2 or 3 substituents selected independently from halogen, CN, nitro, $C_1$-$C_4$-alkyl, $C_1$-$C_4$-haloalkyl, $C_1$-$C_4$-alkoxy and $C_1$-$C_4$-haloalkoxy, where phenyl may have, as substituents, additional $C_3$-$C_8$-cycloalkyl which is unsubstituted or has at least one substituent selected from halogen and $C_3$-$C_8$-cycloalkyl, $R^{1c}$, $R^{1g}$ and $R^{1h}$ are each independently hydrogen, $C_1$-$C_8$-alkyl, $C_1$-$C_8$-haloalkyl, $C_3$-$C_8$-cycloalkyl, $C_1$-$C_4$-alkoxy-$C_1$-$C_4$-alkyl, $C_3$-$C_8$-cycloalkoxy-$C_1$-$C_4$-alkyl, $C_2$-$C_8$-alkenyl, benzyl or phenyl, where the phenyl group in benzyl and phenyl is in each case unsubstituted or has 1, 2 or 3 substituents selected independently from halogen, CN, nitro, $C_1$-$C_4$-alkyl, $C_1$-$C_4$-haloalkyl, $C_1$-$C_4$-alkoxy and $C_1$-$C_4$-haloalkoxy, and $R^{1i}$, $R^{1j}$ are each $C_1$-$C_8$-alkyl, $C_1$-$C_8$-haloalkyl, $C_1$-$C_8$-alkoxy or $C_1$-$C_8$-haloalkoxy;

$R^2$ is hydrogen, $C_1$-$C_4$-alkyl, benzyl or phenyl, where the phenyl group in benzyl and phenyl is in each case unsubstituted or has 1, 2 or 3 substituents selected independently from halogen, CN, nitro, $C_1$-$C_4$-alkyl, $C_1$-$C_4$-haloalkyl, $C_1$-$C_4$-alkoxy and $C_1$-$C_4$-haloalkoxy; and $R^3$ is hydrogen, halogen, $C_1$-$C_8$-alkoxy, $C_1$-$C_8$-haloalkoxy, $C_3$-$C_8$-cycloalkoxy, $C_2$-$C_8$-alkenyloxy, $C_1$-$C_8$-alkylthio, $C_1$-$C_8$-haloalkylthio, $C_3$-$C_8$-cycloalkylthio or $C_2$-$C_8$-alkenylthio;

and to a process for converting such compounds to the corresponding 3-difluoro-methylpyrazol-4-ylcarboxylic acids of the formula (VI)

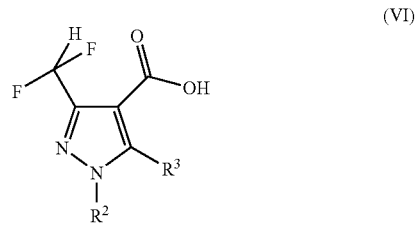

(VI)

in which $R^2$ and $R^3$ have one of the definitions given above.

WO 92/12970 describes (3-difluoromethyl-1-methylpyrazol-4-yl)carboxamides and their use as fungicides. These compounds are prepared starting from a 4,4-difluoroacetoacetic ester which is reacted successively with triethyl orthoformate and with methyl-hydrazine to obtain the (3-difluoromethyl-1-methylpyrazol-4-yl)carboxylic ester. This is subsequently hydrolyzed to the carboxylic acid.

WO 2005/044804 describes carboxylic esters of fluoromethyl-substituted heterocycles including ethyl 3-(difluoromethyl)-1-methyl-1H-pyrazol-4-carboxylate, and also their preparation by halogen exchange on the corresponding carboxylic esters of chloro-methyl-substituted heterocycles.

The processes known to date from the prior art for preparing 3-difluoromethyl-substituted pyrazole compounds either start from starting compounds whose provision is comparatively complicated or expensive, or use, for the introduction of the difluoromethyl group, reagents based on hydrogen fluoride or fluoride, some of which are toxicologically controversial and, owing to their corrosivity, complicate industrial scale implementation. Furthermore, the processes described in the prior art are multistage processes with a multitude of workups and purifications of the intermediates passed through and associated yield losses.

It is thus an object of the present invention to provide a process for preparing 3-difluoromethyl-substituted pyrazole compounds which starts from starting compounds which are available on the industrial scale or whose starting compounds can be prepared readily from products available on the industrial scale. The process should minimize the yield losses associated with the workup and purification of intermediates. Moreover, the use of corrosive fluorine reagents should be avoided.

It has been found that, surprisingly, this object is achieved by a process in which a reaction product (II) which is obtained by reacting a 1-amino-1,1,2,2-tetrafluoroethane of the formula (III) defined below with an acid and subsequent reaction of the resulting intermediate with a base and an ethylene compound of the formula (IV) defined below is reacted with a hydrazine compound.

The present invention thus provides a process for preparing compounds of the formula (I) as defined above, comprising
A) the reaction of a compound of the formula (III)

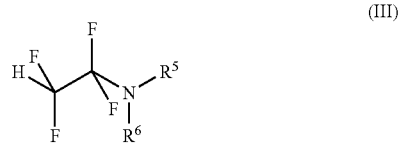

in which
R$^5$ and R$^6$ are each independently C$_1$-C$_8$-alkyl, C$_1$-C$_8$-haloalkyl, C$_3$-C$_8$-cycloalkyl, benzyl or phenyl, where the phenyl group in benzyl and phenyl is in each case unsubstituted or has 1, 2 or 3 substituents selected independently from halogen, CN, nitro, C$_1$-C$_4$-alkyl, C$_1$-C$_4$-haloalkyl, C$_1$-C$_4$-alkoxy and C$_1$-C$_4$-haloalkoxy, or
R$^5$ and R$^6$, together with the nitrogen atom to which they are bonded, are an N-bonded 3- to 8-membered heterocycle which, as well as the nitrogen atom, may also have 1 or 2 further heteroatoms selected from N, O and S as ring atoms and is unsubstituted or has 1, 2, 3 or 4 substituents selected independently from halogen, CN, nitro, C$_1$-C$_4$-alkyl, C$_1$-C$_4$-haloalkyl, C$_1$-C$_4$-alkoxy and C$_1$-C$_4$-haloalkoxy;
with an acid and a compound of the formula (IV)

in which
R$^1$ and R$^3$ are each as defined above and
R$^4$ is halogen, —OR$^{4a}$, —SR$^{4a}$, —O—SO$_2$—R$^{4a}$ or an —NR$^{4b}$R$^{4c}$ group, in which
R$^{4a}$, R$^{4b}$ and R$^{4c}$ are each independently hydrogen, C$_1$-C$_8$-alkyl, C$_1$-C$_8$-haloalkyl, C$_2$-C$_8$-alkenyl, C$_3$-C$_8$-cycloalkyl, benzyl or phenyl, where the phenyl group in benzyl and phenyl is in each case unsubstituted or has 1, 2 or 3 substituents selected independently from halogen, CN, nitro, C$_1$-C$_4$-alkyl, C$_1$-C$_4$-haloalkyl, C$_1$-C$_4$-alkoxy and C$_1$-C$_4$-haloalkoxy, or
R$^{4b}$ and R$^{4c}$, together with the nitrogen atom to which they are bonded, are an N-bonded 3- to 8-membered heterocycle which, as well as the nitrogen atom, may also have 1 or 2 further heteroatoms selected from N, O and S as ring atoms and is unsubstituted or has 1, 2, 3 or 4 substituents selected independently from halogen, CN, nitro, C$_1$-C$_4$-alkyl, C$_1$-C$_4$-haloalkyl, C$_1$-C$_4$-alkoxy and C$_1$-C$_4$-haloalkoxy
to obtain a reaction product (II), and
B) the reaction of the reaction product (II) with a hydrazine compound of the formula H$_2$N—NHR$^2$ in which R$^2$ has one of the definitions given above to obtain a compound of the formula (I).

The process according to the invention affords the compounds of the formula (I) in high yields based on the compounds of the formulae (III) and (IV). The use of corrosive reagents, for example reagents based on hydrogen fluoride or fluoride, can be reduced in this way.

It is assumed that, in step A) of the process according to the invention, the reaction of a compound of the formula (III) with an acid initially forms, by abstraction of a fluoride anion, a reactive iminium ion which, by reaction with a compound of the formula (IV), forms compounds of the formula (II.a) or (II.b)

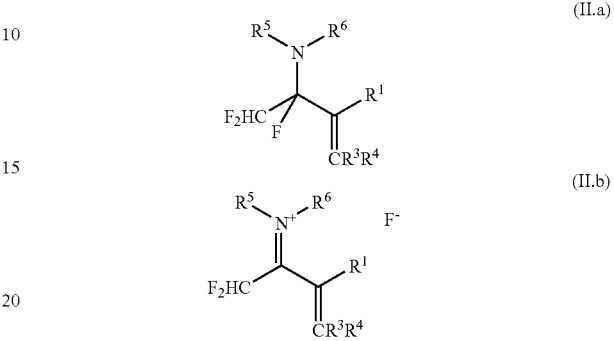

as the reaction product (II), which may be present alongside one another in equilibrium. The Lewis acid adduct of the compound (II.b) has been detected experimentally, for example, with BF$_3$ as the Lewis acid in the form of the tetrafluoroborate. Compounds of the formula (II.a) or (II.b) and Lewis acid adducts of compounds of the formula (II.b), where they are novel, likewise form part of the subject matter of the present invention.

The terms for organic groups used in the definition of the variables, for example the expression "halogen", are collective terms which represent the individual members of these groups of organic units. In the particular case, the prefix C$_x$-C$_y$ denotes the number of possible carbon atoms.

The term "halogen" in each case denotes fluorine, chlorine, bromine or iodine, especially fluorine, chlorine or bromine.

The term "C$_1$-C$_8$-alkyl" denotes a saturated, straight-chain or branched hydrocarbon group comprising from 1 to 8 carbon atoms, especially from 1 to 4 carbon atoms, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethyl-propyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1,1-dimethylpentyl, 1,2-dimethylpentyl, 1,3-dimethylpentyl, 1,4-dimethylpentyl, 2,2-dimethylpentyl, 2,3-dimethylpentyl, 2,4-dimethylpentyl, 3,3-dimethylpentyl, 3,4-dimethylpentyl, 4,4-dimethylpentyl, 1,1,2-trimethylbutyl, 1,1,3-trimethylbutyl, 1,2,2-trimethylbutyl, 1,2,3-trimethylbutyl, 1,3,3-trimethylbutyl, 2,2,3-trimethylbutyl, 2,3,3-trimethylbutyl, 3,3,3-trimethylbutyl, n-octyl, 1-methylheptyl, 2-methylheptyl, 3-methylheptyl, 4-methylheptyl, 5-methylheptyl, 6-methylheptyl, 1,1-dimethylhexyl, 1,2-dimethylhexyl, 1,3-dimethylhexyl, 1,4-dimethylhexyl, 1,5-dimethylhexyl, 2,2-dimethylhexyl, 2,3-dimethylhexyl, 2,4-dimethylhexyl, 2,5-dimethylhexyl, 3,3-dimethylhexyl, 3,4-dimethylhexyl, 3,5-dimethylhexyl, 4,4-dimethylhexyl, 4,5-dimethylhexyl, 5,5-dimethylhexyl and isomers thereof. C$_1$-C$_4$-Alkyl comprises, for example, methyl, ethyl, propyl, 1-methylethyl, butyl, 1-methylpropyl, 2-methylpropyl or 1,1-dimethylethyl.

The term "$C_1$-$C_8$-haloalkyl", as used herein and in the haloalkyl units of $C_1$-$C_8$-halo-alkoxy, denotes straight-chain or branched alkyl groups having from 1 to 8 carbon atoms, where some or all of the hydrogen atoms of these groups are replaced by halogen atoms. $C_1$-$C_4$-Haloalkyl is, for example, chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromo-ethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl.

The term "$C_3$-$C_{12}$-cycloalkyl", preferably "$C_3$-$C_8$-cloalkyl", denotes mono-, bi- or tricyclic hydrocarbon radicals comprising from 3 to 12 carbon atoms, preferably from 3 to 8 carbon atoms, especially from 3 to 6 carbon atoms. Examples of monocyclic radicals comprise cyclopropyl, cyclobutyl, cyclopentyl, cyclohexyl, cycloheptyl or cyclooctyl. Examples of bicyclic radicals comprise bicyclo[2.2.1]heptyl, bicyclo[3.1.1]heptyl, bicyclo[2.2.2]octyl and bicyclo[3.2.1]octyl. Examples of tricyclic radicals are adamantyl and homoadamantyl.

The term "$C_2$-$C_8$-alkenyl" denotes straight-chain and branched unsaturated hydrocarbon radicals comprising from 2 to 8 carbon atoms and at least one carbon-carbon double bond, for example ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-methyl-1-hexenyl, 1-methyl-2-hexenyl, 1-methyl-3-hexenyl, 1-methyl-4-hexenyl, 1-methyl-5-hexenyl, 2-methyl-1-hexenyl, 2-methyl-2-hexenyl, 2-methyl-3-hexenyl, 2-methyl-4-hexenyl, 2-methyl-5-hexenyl, 3-methyl-1-hexenyl, 3-methyl-2-hexenyl, 3-methyl-3-hexenyl, 3-methyl-4-hexenyl, 3-methyl-5-hexenyl, 4-methyl-1-hexenyl, 4-methyl-2-hexenyl, 4-methyl-3-hexenyl, 4-methyl-4-hexenyl, 4-methyl-5-hexenyl, 5-methyl-1-hexenyl, 5-methyl-2-hexenyl, 5-methyl-3-hexenyl, 5-methyl-4-hexenyl, 5-methyl-5-hexenyl, 1-octenyl, 2-octenyl, 3-octenyl, 4-octenyl, 5-octenyl, 6-octenyl, 7-octenyl, 1-methyl-1-heptenyl, 1-methyl-2-heptenyl, 1-methyl-3-heptenyl, 1-methyl-4-heptenyl, 1-methyl-5-heptenyl, 1-methyl-6-heptenyl, 2-methyl-1-heptenyl, 2-methyl-2-heptenyl, 2-methyl-3-heptenyl, 2-methyl-4-heptenyl, 2-methyl-5-heptenyl, 2-methyl-6-heptenyl, 3-methyl-1-heptenyl, 3-methyl-2-heptenyl, 3-methyl-3-heptenyl, 3-methyl-4-heptenyl, 3-methyl-5-heptenyl, 3-methyl-6-heptenyl, 4-methyl-1-heptenyl, 4-methyl-2-heptenyl, 4-methyl-3-heptenyl, 4-methyl-4-heptenyl, 4-methyl-5-heptenyl, 4-methyl-6-heptenyl, 5-methyl-1-heptenyl, 5-methyl-2-heptenyl, 5-methyl-3-heptenyl, 5-methyl-4-heptenyl, 5-methyl-5-heptenyl, 5-methyl-6-heptenyl, 6-methyl-1-heptenyl, 6-methyl-2-heptenyl, 6-methyl-3-heptenyl, 6-methyl-4-heptenyl, 6-methyl-5-heptenyl, 6-methyl-6-heptenyl and isomers thereof.

The term "$C_1$-$C_8$-alkoxy" denotes straight-chain or branched saturated alkyl groups comprising from 1 to 8 carbon atoms, which are bonded via an oxygen atom. Examples comprise $C_1$-$C_6$-alkoxy, for example methoxy, ethoxy, $OCH_2$—$C_2H_5$, $OCH(CH_3)_2$, n-butoxy, $OCH(CH_3)$—$C_2H_5$, $OCH_2$—$CH(CH_3)_2$, $OC(CH_3)_3$, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, n-heptyloxy, 1-methylhexyloxy, 2-methylhexyloxy, 3-methylhexyloxy, 4-methylhexyloxy, 5-methylhexyloxy, 1,1-dimethylpentyloxy, 1,2-dimethylpentyloxy, 1,3-dimethylpentyloxy, 1,4-dimethylpentyloxy, 2,2-dimethylpentyloxy, 2,3-dimethylpentyloxy, 2,4-dimethylpentyloxy, 3,3-dimethylpentyloxy, 3,4-dimethylpentyloxy, 4,4-dimethylpentyloxy, 1,1,2-trimethylbutyloxy, 1,1,3-trimethylbutyloxy, 1,2,2-trimethylbutyloxy, 1,2,3-trimethylbutyloxy, 1,3,3-trimethylbutyloxy, 2,2,3-trimethylbutyloxy, 2,3,3-trimethylbutyloxy, 3,3,3-trimethylbutyloxy, n-octyloxy, 1-methylheptyloxy, 2-methylheptyloxy, 3-methylheptyloxy, 4-methylheptyloxy, 5-methylheptyloxy, 6-methylheptyloxy, 1,1-dimethylhexyloxy, 1,2-dimethylhexyloxy, 1,3-dimethylhexyloxy, 1,4-dimethylhexyloxy, 1,5-dimethylhexyloxy, 2,2-dimethylhexyloxy, 2,3-dimethylhexyloxy, 2,4-dimethylhexyloxy, 2,5-dimethylhexyloxy, 3,3-dimethylhexyloxy, 3,4-dimethylhexyloxy, 3,5-dimethylhexyloxy, 4,4-dimethylhexyloxy, 4,5-dimethylhexyloxy, 5,5-dimethylhexyloxy and isomers thereof. $C_1$-$C_4$-Alkoxy comprises, for example, methoxy, ethoxy, propoxy, 1-methylethoxy, butoxy, 1-methyl-propoxy, 2-methylpropoxy or 1,1-dimethylethoxy.

The term "$C_1$-$C_4$-alkoxy-$C_1$-$C_4$-alkyl" denotes $C_1$-$C_4$-alkyl radicals where a carbon atom is bonded to a $C_1$-$C_4$-alkoxy radical. Examples thereof are $CH_2$—$OCH_3$, $CH_2$—$OC_2H_5$, n-propoxymethyl, $CH_2$—$OCH(CH_3)_2$, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methyl-propoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methyl-propoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)-butyl, 2-(2-methylpropoxy)butyl, 2-(1,1- dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl.

In the context of the present invention, the term "hetaryl" comprises unsubstituted or substituted, heteroaromatic, mono- or bicyclic groups having from 5 to 10 ring atoms, preferably monocyclic groups having 5 or 6 ring atoms, in which 1, 2, 3 or 4 of the ring carbon atoms are replaced by heteroatoms selected from O, N and S. Examples of hetaryl are furyl, thienyl, oxazolyl, isoxazolyl, thiazolyl, isothiazolyl, benzofuranyl, benzthiazolyl, benzimidazolyl, pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl and carbazolyl, where these heterocycloaromatic groups, in the case of substitution, may bear generally 1, 2 or 3 substituents. The substituents are generally selected from halogen, cyano, nitro, $C_1$-$C_4$-alkyl, $C_1$-$C_4$-alkoxy, $C_1$-$C_4$-halo-alkyl, or $C_1$-$C_4$-haloalkoxy.

The term "N-bonded 3- to 8-membered heterocycle" denotes nitrogen-containing cyclic groups having from 3 to 8 ring atoms, preferably having 5 or 6 ring atoms, which are bonded to the remaining part of the compound via a ring nitrogen atom, where the ring, as well as the ring nitrogen atom via which it is bonded, optionally has 1 or 2 further heteroatoms as ring atoms, which are selected from N, O and S, and where the ring is unsubstituted or has 1, 2 or 3 substituents selected from halogen, CN, nitro, $C_1$-$C_4$-alkyl, $C_1$-$C_4$-haloalkyl, $C_1$-$C_4$-alkoxy and $C_1$-$C_4$-haloalkoxy.

Examples of N-bonded heterocycles are pyrrolyl, pyrazolyl, imidazolyl, triazolyl, pyrrolidinyl, pyrazolinyl, pyrazolidinyl, imidazolinyl, imidazolidinyl, piperidinyl, piperazinyl, morpholinyl, each of which are bonded to the rest of the compound via a ring nitrogen atom and are unsubstituted or have 1, 2 or 3 substituents selected from halogen, CN, nitro, $C_1$-$C_4$-alkyl, $C_1$-$C_4$-haloalkyl, $C_1$-$C_4$-alkoxy and $C_1$-$C_4$-haloalkoxy.

With regard to the process according to the invention, at least one of the $R^1$, $R^{1a}$, $R^{1b}$, $R^{1c}$, $R^{1d}$, $R^{1e}$, $R^{1f}$, $R^{1g}$, $R^{1h}$, $R^{1i}$, $R^{1j}$, $R^2$, $R^3$, $R^4$, $R^{4a}$, $R^{4b}$, $R^{4c}$, $R^5$ or $R^6$ radicals preferably has one of the definitions given below. More preferably, all of the aforementioned radicals have one of the definitions given below.

$R^1$ in the compounds of the formula (I) and in the starting compounds used to prepare them is preferably hydrogen, $C_1$-$C_8$-alkyl, phenyl, cyano or a —C(=O)—$OR^{1a}$ group, where phenyl is unsubstituted or has 1 or 2 substituents selected from halogen, nitro, $C_1$-$C_4$-alkyl, $C_1$-$C_4$-haloalkyl or $C_1$-$C_4$-alkoxy. $R^1$ is more preferably a —C(=O)—$OR^{1a}$ group.

$R^{1a}$, $R^{1d}$, $R^{1e}$ and $R^{1f}$ are preferably each $C_1$-$C_8$-alkyl or $C_3$-$C_8$-cycloalkyl.

$R^{1b}$ is preferably hydrogen, $C_1$-$C_8$-alkyl or $C_3$-$C_8$-cycloalkyl.

$R^{1c}$, $R^{1g}$ and $R^{1h}$ are preferably each hydrogen, $C_1$-$C_4$-alkyl or $C_3$-$C_8$-cycloalkyl.

$R^{1i}$ and $R^{1j}$ are preferably each $C_1$-$C_8$-alkyl or $C_1$-$C_8$-alkoxy.

$R^2$ in the hydrazine compounds used in accordance with the invention and accordingly in the compounds of the formula (I) is preferably hydrogen, methyl, benzyl or phenyl, where the phenyl groups in the two latter groups is unsubstituted or has 1 or 2 substituents selected from halogen, nitro, $C_1$-$C_4$-alkyl or $C_1$-$C_4$-alkoxy. $R^2$ is more preferably methyl.

$R^3$ in the compounds of the formula (I) and in the starting compounds used to provide them is preferably hydrogen, halogen or $C_1$-$C_4$-alkoxy. $R^3$ is more preferably hydrogen.

$R^4$ in the compounds of the formula (IV) and consequently in the reaction products (II) prepared therefrom is preferably —$OR^{4a}$, —$SR^{4a}$ or an —$NR^{4b}R^{4c}$ group, in which $R^{4a}$, $R^{4b}$ and $R^{4c}$ each have one of the definitions given above. Likewise preferably, $R^4$ in the compounds of the formula (IV) and consequently in the reaction products (II) prepared therefrom is halogen, —$OR^{4a}$, —$SR^{4a}$ or —O—$SO_2$—$R^{4a}$, in which $R^{4a}$ has one of the definitions given above. $R^4$ is more preferably —$OR^{4a}$ or an —$NR^{4b}R^{4c}$ group, in which $R^{4a}$, $R^{4b}$ and $R^{4c}$ have one of the definitions given above. $R^4$ in the compounds of the formula (IV) and consequently in the reaction products (II) prepared therefrom is most preferably —$OR^{4a}$ in which $R^{4a}$ has one of the definitions given above.

$R^{4a}$, $R^{4b}$ and $R^{4c}$ in the compounds of the formula (IV) and consequently in the reaction products (II) prepared therefrom is hydrogen, $C_1$-$C_4$-alkyl, $C_1$-$C_4$-haloalkyl or phenyl which is unsubstituted or has 1 or 2 substituents selected from halogen, nitro, $C_1$-$C_4$-alkyl and $C_1$-$C_4$-haloalkyl, $C_1$-$C_4$-alkoxy; or Rob and Roc, together with the nitrogen atom to which they are bonded, are each a 5- to 6-membered N-bonded heterocycle which, as well as the nitrogen atom, may also have one further nitrogen or oxygen ring atom and is unsubstituted or has 1 or 2 substituents selected from halogen, nitro, $C_1$-$C_4$-alkyl or $C_1$-$C_4$-haloalkyl.

$R^5$ and $R^6$ in the compounds of the formula (III) and consequently in the reaction products (II) prepared are preferably each independently $C_1$-$C_8$-alkyl, $C_3$-$C_8$-cycloalkyl or phenyl, or $R^5$ and $R^6$, together with the nitrogen atom to which they are bonded, are an N-bonded 5- or 6-membered heterocycle as defined above. More preferably, $R^5$ and $R^6$ are each $C_1$-$C_4$-alkyl or, together with the nitrogen atom, are an N-bonded 5- or 6-membered heterocycle. Most preferably, $R^5$ and $R^6$ are each methyl or ethyl or, together with the nitrogen atom, are piperidin-1-yl, 4-methylpiperazin-1-yl or morpholin-4-yl.

In the reaction of a reaction product (II) with a hydrazine compound of the formula $R^2HN$—$NH_2$ in step B) of the process according to the invention, the procedure will generally be to initially charge the reaction product (II), if appropriate in a suitable solvent or as a reaction mixture comprising the reaction product (II), and to add the hydrazine compound, if appropriate in a suitable solvent.

Alternatively, the hydrazine compound, if appropriate in a suitable solvent, can be initially charged, and the reaction product (II), if appropriate in a suitable solvent or as a reaction mixture comprising the reaction product (II), can be added.

Typically, in step B) of the process according to the invention, the hydrazine compound of the formula $R^2HN$—$NH_2$ will be used in an amount of from 0.5 to 3 mol, preferably from 0.7 to 1.5 mol and more preferably from 0.9 to 1.2 mol, based on one mole of the reaction product (II) or on one mole of the compounds of the formula (III) or (IV) used to prepare it.

Preference is given to performing the reaction of the reaction product (II) with a hydrazine compound of the formula $R^2HN$—$NH_2$ at temperatures of from −80 to 30° C. and especially at temperatures of form −50 to 10° C.

The hydrazine compounds of the formula $R^2HN$—$NH_2$ may be used in step B) of the process according to the invention in pure form or in the form of their solvates, for example in the form of their hydrates.

Preference is given to using the hydrazine compounds of the formula $R^2HN$—$NH_2$ or solvate thereof in step B) of the process according to the invention as a solution in a suitable inert solvent. A solution of the hydrazine compound in the solvent used for the reaction will preferably be used. Suitable solvents are those mentioned hereinafter: water, aqueous bases such as sodium hydroxide solution or potassium hydroxide solution, or organic solvents, especially ethers, such as diethyl ether, diisopropyl ether, methyl tert-butyl ether, tetrahydrofuran, dioxane or anisole, nitriles such as acetonitrile or propionitrile, ketones such as acetone, methyl ethyl ketone, diethyl ketone or methyl tert-butyl ketone, alcohols such as methanol, ethanol, n-propanol, iso-propanol, n-butanol or tert-butanol, dimethyl sulfoxide, dimethylformamide, N-methylpyrrolidinone (NMP), 1,3-dimethyl-2-imidazolidinone (DMI), dimethylacetamide, dimethylethyleneurea, dimethylpropyleneurea (DMPU) or tetramethylurea, or mixtures of the aforementioned solvents.

Preferred solvents are water, $C_1$-$C_4$-alcohols, aqueous bases or mixtures of these solvents.

Suitable hydrazine compounds of the formula $R^2HN$—$NH_2$ are especially hydrazine or hydrazine hydrate, methylhydrazine, ethylhydrazine, phenylhydrazine, chlorophenylhydrazine, bromophenylhydrazine, nitrophenylhydrazine, dinitrophenylhydrazine, tolylhydrazine, benzylhydrazine or nitrobenzylhydrazine. In the process according to the invention, particular preference is given to using methylhydrazine as the hydrazine compound of the formula $R^2HN$—$NH_2$.

A compound of the formula (III) can be reacted in step A) of the process according to the invention, for example, with a Brönsted acid. Suitable Brönsted acids are, for example, HF, HCl, HBr, $H_2SO_4$, sulfonic acids such as methanesulfonic acid, benzenesulfonic acid, p-toluenesulfonic acid, trifluoromethanesulfonic acid or tetrafluoroethanesulfonic acid or fluorinated carboxylic acids such as trifluoroacetic acid.

Typically, the procedure in step A) of the process according to the invention in the reaction of a compound of the formula (III) with an acid will be to initially charge the compound of the formula (III), if appropriate in a suitable solvent, or as a reaction mixture comprising the compound of the formula (III), and to add the acid, if appropriate in a suitable solvent.

Typically, in step A) of the process according to the invention, the acid will be used in an amount of from 0.01 to 4 mol, preferably from 0.5 to 3 mol, more preferably from 0.8 to 2.5 mol, and most preferably from 0.9 to 2.2 mol, based on one mole of the compound of the formula (III).

Preference is given to performing the reaction of a compound of the formula (III) with an acid at temperatures of from −80 to 100° C. and especially at temperatures of from −10 to 30° C.

However, the compound of the formula (III) will preferably be reacted in step A) of the process according to the invention with a Lewis acid.

The reaction of a compound of the formula (III) with a Lewis acid with abstraction of a fluoride anion is known per se and is described, for example, in Journal of the Chemical Society, Chemical Communications 1975, 956.

Typically, the procedure in the reaction of a compound of the formula (III) with a Lewis acid in step A) of the process according to the invention will be to initially charge the compound of the formula (III), if appropriate in a suitable solvent, or as a reaction mixture comprising the compound of the formula (III), and to add the Lewis acid, if appropriate in a suitable solvent.

Typically, in step A) of the process according to the invention, the Lewis acid will be used in an amount of from 0.01 to 4 mol, preferably from 0.5 to 3 mol, more preferably from 0.8 to 2.5 mol, and most preferably from 0.9 to 2.2 mol, based on one mole of the compound of the formula (III).

Preference is given to performing the reaction of a compound of the formula (III) with a Lewis acid at temperatures of from −80 to 100° C. and especially at temperatures of from −10 to 30° C.

The Lewis acids may be used in step A) of the process according to the invention in pure form or in the form of their complexes, for example in the form of their etherates. Suitable Lewis acids are, for example, compounds of the formulae LiX, $MgX_2$, $CaX_2$, $BX_3$, $R^{LS}$—$BX_2$, $(R^{LS})_2BX$, $(R^{LS})_3B$, $AlX_3$, $R^{LS}$—$AlX_2$, $(R^{LS})_2AlX$, $(R^{LS})_3Al$, $ScX_3$, $TiX_4$, $R^{LS}OTiX_3$, $(R^{LS}O)_2TiX_2$, $(R^{LS}O)_3TiX$, $(R^{LS}O)_4Ti$, $ZrX_4$, $FeX_3$, $NiX_2$, $CuX$, $CuX_2$, $ZnX_2$, $TiX_4$, $R^{LS}OSiX_3$, $(R^{LS}O)_2SiX_2$, $(R^{LS}O)_3SiX$, $SnX_4$, $GeX_4$, $PX_5$, $AsX_5$, $SbX_5$, $BiX_3$, in which X is halogen, CN, trifluoromethylsulfonate or OH, and $R^{LS}$ is $C_1$-$C_4$-alkyl, or mixtures of the aforementioned Lewis acids. X is preferably F, Cl or trifluoromethylsulfonate. $R^{LS}$ is preferably methyl (Me), ethyl or isopropyl. Preferred Lewis acids are $MgF_2$, $MgCl_2$, $CaCl_2$, $BF_3$, $B(OH)_3$, $AlCl_3$, $MeAlCl_2$, $Me_2AlCl$, $SiCl_4$, $Me_3SiCl$, $TiCl_4$ and $ZnCl_2$. A particularly preferred Lewis acid is $BF_3$. Examples of preferred complexes are $BF_3$-diethyl etherate, $BF_3$-dimethyl etherate, $BF_3$-tetrahydrofuranate or $BF_3$-amine complexes such as the $BF_3$-pyridine complex.

Preference is given to using the Lewis acid or solvate thereof in step A) of the process according to the invention as a solution in a suitable inert solvent. A solution of the Lewis acid in the solvent used for the reaction will preferably be used. Preferred solvents are those mentioned hereinafter.

Suitable solvents for step A) of the process according to the invention are generally aprotic organic solvents. Examples are aromatic hydrocarbons such as toluene, o-xylene, m-xylene or p-xylene, halogenated hydrocarbons such as methylene chloride, chloroform or chlorobenzene, ethers such as diethyl ether, diisopropyl ether, methyl tert-butyl ether, cyclopentyl methyl ether, tetrahydrofuran, 2-methyltetrahydrofuran, dioxane or anisole, nitriles such as acetonitrile or propionitrile, ketones such as acetone, methyl ethyl ketone, diethyl ketone or methyl tert-butyl ketone, dimethyl sulfoxide, dimethylformamide, N-methylpyrrolidinone (NMP), 1,3-dimethyl-2-imido-azolidinone (DMI), dimethylacetamide, dimethylethyleneurea, dimethylpropyleneurea (DMPU) or tetramethylurea, or mixtures of the aforementioned solvents. Preferred solvents are ethers, especially diethyl ether, tetrahydrofuran, dioxane and mixtures thereof.

Preference is given to performing step A) of the process according to the invention in the substantial absence of water, i.e. in a dry organic solvent. Here and hereinafter, "dry" means that the solvent has a water content of at most 500 ppm and especially of at most 100 ppm. In addition, it may be advantageous, for the exclusion of water, to perform step A) of the process according to the invention under protective gas atmosphere, for example under nitrogen atmosphere.

It is assumed that the reaction of a compound of the formula (III) with an acid in step A) of the process according to the invention, through abstraction of a fluoride ion, forms a reactive iminium ion of the following formula

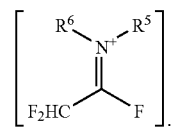

This reactive reaction product is preferably used without preceding isolation in the reaction step which follows.

In a preferred embodiment of the process according to the invention, the reaction mixture obtained by the process according to the invention in the reaction of a compound of the formula (III) with an acid, comprising a reactive reaction product, is therefore reacted without preceding isolation with a compound of the formula (IV).

Typically, the product obtained in the reaction of a compound of the formula (III) with an acid will be initially charged, if appropriate as a reaction mixture, and the compound of the formula (IV), if appropriate in a suitable solvent, will be added.

Typically, in step A) of the process according to the invention, the compound of the formula (IV) will be used in an amount of from 0.5 to 3 mol, preferably from 0.7 to 2 mol and more preferably from 0.8 to 1.2 mol, based on one mole of the reaction product (II) or based on one mole of the compound of the formula (III) used. Based on the overall yield of the process according to the invention, it has been found to be particularly advantageous to use the compound of the formula (IV) in deficiency based on the compound of the formula (III), i.e. less than 1 mol of the compound of the formula (IV) based on one mole of the compound (III).

Preference is given to performing the reaction of the product obtained by reaction of a compound of the formula (III) with an acid with a compound of the formula (IV) in step A) of the process according to the invention at temperatures of from −10 to 100° C. and especially at temperatures of from 0 to 40° C.

Especially suitable are compounds of the formula (IV) in which $R^1$ is a hydrolyzable CN, $C(=O)-OR^{1a}$, $C(=O)NR^{1b}R^{1c}$, $C(=O)-SR^{1d}$ or $C(=S)-SR^{1e}$ radical and especially a $C(=O)-OR^{1a}$ radical, in which $R^{1a}$, $R^{1b}$, $R^{1c}$, $R^{1d}$ and $R^{1e}$ each have one of the definitions given above. Likewise suitable are compounds of the formula (IV) in which $R^1$ is an inert radical, for example hydrogen, $C_1$-$C_8$-alkyl or optionally substituted phenyl, and is especially hydrogen. Likewise especially suitable are compounds of the formula (IV) in which $R^4$ is $-OR^{4a}$; such compounds are also referred to hereinafter as enol ethers.

In a specific embodiment of the process according to the invention, the reaction with a compound of the formula (IV) is performed without adding a base other than the compound of the formula (III) and the reaction product thereof.

In another specific embodiment of the process according to the invention, the reaction of a compound of the formula (IV) is performed additionally in the presence of a suitable base. The base is added preferably before or simultaneously with the addition of the compound of the formula (IV).

Suitable bases used additionally in step A) of the process according to the invention are organic bases in general. Suitable bases are especially tertiary amines, for example tri($C_1$-$C_6$-alkyl)amines such as trimethylamine, triethylamine or diisopropyl-ethylamine, cyclic amines such as N-methylpiperidine, aromatic amines such as pyridine, 2,4,6-trimethylpyridine (collidine), 2,6-dimethylpyridine (lutidine), 2-methylpyridine (2-picoline), 3-methylpyridine (3-picoline) or 4-dimethylaminopyridine, and also bicyclic amines such as 1,4-diazabicyclo[2.2.2]octane, 1,8-diazabicyclo[5.4.0]undec-7-ene or 1,5-diazabicyclo[4.3.0]non-5-ene. Preference is given to using aromatic amines, particular preference to using pyridine, picoline, lutidine or collidine.

The bases are used generally in an amount of from 0.9 to 2 mol, based on 1 mol of the compounds of the formula (III), preferably in an amount of from 0.95 to 1.5 mol, based on 1 mol of the compounds of the formula (III). However, they may in principle also be used in a greater excess.

Advantageously, the reaction mixture obtained in step A) of the process according to the invention, comprising a reaction product (II), can be used in step B) of the process without preceding workup. In a specific embodiment of the process according to the invention, accordingly, the reaction product (II) obtained in step A) of the process according to the invention will be reacted without preceding isolation with the hydrazine compound of the formula $H_2N-NHR^2$.

In a preferred embodiment of the process according to the invention, the product obtained by reaction of a compound of the formula (III) with an acid and the reaction product (II) prepared therefrom by reaction with a compound of the formula (IV) will be used without preceding isolation in the process for preparing compounds of the formula (I).

Compounds of the formula (III) can be provided, for example, by reacting a secondary amine of the formula (V)

in which $R^5$ and $R^6$ each have one of the definitions given above with tetrafluoroethylene to obtain a compound of the formula (III).

The reaction of 1,1,2,2-tetrafluoroethylene with secondary amines is known per se and is described, for example, in J. Fluorine Chem. 2001, 109, p. 25-31 or J. Am. Chem. Soc. 1960, 82, 5116.

Typically, the procedure in the reaction of 1,1,2,2-tetrafluoroethylene with a secondary amine will be to initially charge the secondary amine and to add 1,1,2,2-tetrafluoroethylene. The reaction is preferably performed in substance, i.e. without addition of a solvent. In the course of the preparation of the compound of the formula (III) and of the further use, suitable measures should be taken for protection from the decomposition of the compound of the formula (III).

Typically, in the reaction of 1,1,2,2-tetrafluoroethylene with a secondary amine, 1,1,2,2-tetrafluoroethylene will be used in an amount of from 0.5 to 2 mol, preferably from 0.8 to 1.2 mol and more preferably from 0.9 to 1.1 mol, based on one mole of the secondary amine used.

Preference is given to performing the reaction of 1,1,2,2-tetrafluoroethylene with a secondary amine at temperatures of from −20 to 60° C. and especially at temperatures of from −10 to 30° C.

Preferred secondary amines for the reaction with 1,1,2,2-tetrafluoroethylene are, for example, di($C_1$-$C_4$-alkyl)amines such as dimethylamine, diethylamine or diisopropylamine.

Advantageously, the reaction mixture obtained in the reaction of the secondary amine with 1,1,2,2-tetrafluoroethylene, comprising the compounds of the formula (III), can be used without preceding workup in step A) of the process according to the invention. In a preferred embodiment of the processes according to the invention, accordingly, the compounds of the formula (III) obtained in the reaction of the secondary amine with 1,1,2,2-tetrafluoroethylene are reacted with an acid without preceding isolation.

In a specific embodiment of the process according to the invention, the $R^1$ radicals are selected from groups which can be converted to a carboxyl group by hydrolysis. These hydrolyzable $R^1$ radicals are referred to hereinafter as $R^{1'}$ radicals. The $R^{1'}$ radicals are selected from CN, $-C(=O)-OR^{1aa}$, $-C(=O)-NR^{1bb}R^{1cc}$, $-C(=O)-SR^{1dd}$ and $-C(=S)-$ $SR^{1ee}$, where $R^{1aa}$, $R^{1bb}$, $R^{1cc}$, $R^{1dd}$ and $R^{1ee}$ each have one of the definitions given above for the corresponding $R^{1a}$, $R^{1b}$, $R^{1c}$, $R^{1d}$ and $R^{1e}$ radicals.

Compounds of the formula (I) in which $R^1$ is a hydrolyzable radical, i.e. $R^1$ has one of the definitions given for $R^{1'}$, can be converted by hydrolysis to the corresponding 3-difluoromethylpyrazole-4-carboxylic acids.

Accordingly, the present invention further relates to a process for preparing compounds of the formula (VI), as defined above, comprising i) the preparation of a compound of the formula (I.a) by a process according to the invention described above for the preparation of compounds of the formula (I),

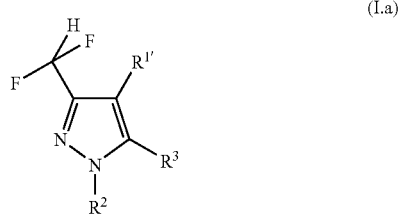

(I.a)

in which
$R^{1'}$ is CN, $-C(=O)-OR^{1aa}$, $-C(=O)-NR^{1bb}R^{1cc}$, $-C(=O)-SR^{1dd}$ or $-C(=S)-SR^{1ee}$, where $R^{1aa}$, $R^{1dd}$ and $R^{1ee}$ are each independently $C_1$-$C_8$-alkyl, $C_1$-$C_8$-haloalkyl, $C_3$-$C_8$-cycloalkyl, $C_1$-$C_4$-alkoxy-$C_1$-$C_4$-alkyl, $C_3$-$C_8$-cycloalkoxy-$C_1$-$C_4$-alkyl, $C_2$-$C_8$-alkenyl, benzyl or phenyl, $R^{1bb}$ and $R^{1cc}$ are each independently hydrogen, $C_1$-$C_8$-alkyl, $C_1$-$C_8$-haloalkyl or $C_3$-$C_8$-cycloalkyl, benzyl or phenyl, and where the phenyl group in benzyl and phenyl is in each case unsubstituted or has 1, 2 or 3 substituents each independently selected from halogen, CN, nitro, $C_1$-$C_4$-alkyl, $C_1$-$C_4$-haloalkyl, $C_1$-$C_4$-alkoxy and $C_1$-$C_4$-haloalkoxy, and
$R^2$ and $R^3$ has one of the definitions given above; and ii) the hydrolysis of a compound of the formula (I.a) to obtain a compound of the formula (VI).

The hydrolysis can be performed under acidic conditions, basic conditions or in another manner. The compound of the formula (I) can be used as such, i.e. after isolation. However, it is also possible to use the reaction mixture obtained in step B) of the process according to the invention for preparing compounds of the formula (I), if appropriate after removal of volatile constituents such as solvents, without further purification for the hydrolysis.

For the basic hydrolysis of the compound of the formula (I), the compound of the formula (I) will typically be treated with an alkali metal hydroxide such as sodium hydroxide, potassium hydroxide or lithium hydroxide, preferably with an aqueous solution of an alkali metal hydroxide, especially with sodium hydroxide solution or potassium hydroxide solution, until complete hydrolysis of the ester. Likewise preferred are solutions of alkali metal hydroxide in $C_1$-$C_4$-alkanols, especially in methanol.

In the basic hydrolysis, the molar ratio of compound of the formula (I) to base is usually in the range from 1:0.8 to 1:10 and is especially about equimolar (i.e. it is in the range from 0.9:1 to 1.2:1); however, a greater base excess, for example up to 5 mol of the base per mole of the compound of the formula (I), may also be advantageous.

Typically, the basic hydrolysis is effected in a diluent or solvent. Suitable diluents or solvents, as well as water, are also organic solvents which are stable toward alkali, and mixtures thereof with water. Examples of alkali-stable organic solvents are especially the aforementioned $C_1$-$C_4$-alcohols and the aforementioned acyclic and cyclic ethers. Preference is given to performing the hydrolysis in aqueous phase, i.e. in water or a mixture of water with one of the aforementioned organic solvents, in which case the content of organic solvent in the aqueous phase, in general, typically does not exceed 30% by volume, based on the total amount of water and organic solvent.

Preference is given to performing the basic hydrolysis at temperatures of from 0 to 80° C., more preferably at from 10 to 60° C. In general, the upper temperature limit is the boiling point of the solvent used when the reaction is conducted at ambient pressure. The reaction time is dependent on the reaction temperature, the concentration and the stability of the particular ester bond. In general, the reaction conditions are selected such that the reaction time is in the range from 1 to 12 h, especially in the range from 2 to 8 h.

The acid hydrolysis of a compound of the formula (I) can be performed in analogy to known acidic ester hydrolyses, i.e. in the presence of catalytic or stoichiometric amounts of an acid and water (see, for example, J. March, Advanced Organic Chemistry, 2nd Ed., 334-338, McGraw-Hill, 1977 and literature cited there). Frequently, the reaction will be performed in a mixture of water and an aprotic organic solvent, for example an ether. Examples of suitable acids are hydrohalic acids, sulfuric acid, organic sulfonic acids such as p-toluenesulfonic acid, methanesulfonic acid, phosphoric acid and acidic ion exchange resins and the like.

Suitable hydrolysis catalysts are also alkali metal iodides such as lithium iodide, sodium iodide or potassium iodide, trimethyliodosilane, or mixtures of trimethylchlorosilane with alkali metal iodides.

The compound of the formula (VI) is isolated by customary separating processes, for example precipitation by adjusting the pH or by extraction.

In a preferred embodiment of the process for preparing a compound of the formula (VI), the compound of the formula (I.a) prepared in step B) of the process according to the invention for preparing a compound of the formula (I) is used without preceding isolation in step ii) of the inventive.

$R^{1'}$ in the compounds of the formula (I.a) is preferably a CN, $-C(=O)-OR^{1aa}$ or $-C(=O)-NR^{1bb}R^{1cc}$ group and more preferably $-C(=O)-OR^{1aa}$. $R^{1aa}$ herein is especially $C_1$-$C_6$-alkyl such as methyl or ethyl. $R^{1bb}$ and $R^{1cc}$ herein are especially hydrogen or $C_1$-$C_6$-alkyl such as methyl or ethyl.

With regard to the preferred $R^2$ and $R^3$ radicals, the same applies as was stated above in the context of the process according to the invention for preparing compounds of the formula (I).

The compounds of the formula (VI) obtained by hydrolysis are advantageously suitable for preparing a multitude of active pharmaceutical and phytosanitary ingredients, for example for preparing 3-difluoromethylpyrazole-4-carboxamides, as described, inter alia, in EP 0589301, WO 03/070705, WO 03/074491, WO 05123690 or WO 06/087343.

Suitable methods for preparing carboxamides by reacting carboxylic acids and derivatives thereof with amines are known to those skilled in the art, for example from the prior art cited at the outset and from J. March, Advanced Organic Chemistry, 2nd Ed., 382 ff, McGraw-Hill, 1977, and Organikum, 21st edition, Wiley-VCH, Weinheim 2001, p. 481-484 and literature cited there.

Examples of 3-difluoromethylpyrazole-4-carboxamides whose starting compounds of the formulae (I) and (VI) can be prepared by the above-described processes according to the invention are: N-(2-bicyclopropyl-2-ylphenyl)-3-difluoromethyl-1-methylpyrazol-4-ylcarboxamide, N-(3',4',5'-trifluorobiphenyl-2-yl)-3-difluoromethyl-1-methylpyrazol-4-ylcarboxamide, N-(2',4',5'-trifluorobiphenyl-2-yl)-3-difluoromethyl-1-methylpyrazol-4-ylcarboxamide, N-(3',4'-dichloro-3-fluorobiphenyl-2-yl)-1-methyl-3-difluoromethyl-1H-pyrazol-4-ylcarboxamide, N-(3',4'-difluoro-3-fluorobiphenyl-2-yl)-1-methyl-3-difluoromethyl-1H-pyrazol-4-ylcarboxamide, N-(3'-chloro-4'-fluoro-3-fluorobiphenyl-2-yl)-1-methyl-3-difluoromethyl-1H-pyrazol-4-ylcarboxamide, N-(3',4'-dichloro-4-fluorobiphenyl-2-yl)-1-methyl-3-difluoromethyl-1H-pyrazol-4-ylcarboxamide, N-(3',4'-difluoro-4-fluorobiphenyl-2-yl)-1-methyl-3-difluoromethyl-1H-pyrazol-4-ylcarboxamide, N-(3'-chloro-4'-fluoro-4-fluorobiphenyl-2-yl)-1-methyl-3-difluoromethyl-1H-pyrazol-4-ylcarboxamide, N-(3',4'-dichloro-5-fluorobiphenyl-2-yl)-1-methyl-3-difluoromethyl-1H-pyrazol-4-ylcarboxamide, N-(3',4'-difluoro-5-fluorobiphenyl-2-yl)-1-methyl-3-difluoromethyl-1H-pyrazol-4-ylcarboxamide, N-(3'-chloro-4'-fluoro-5-fluorobiphenyl-2-yl)-1-methyl-3-difluoromethyl-1H-pyrazol-4-ylcarboxamide, N-[2-(1,1,2,3,3,3-hexafluoropropoxy)phenyl]-3-difluoromethyl-1-methyl-1H-pyrazol-4-ylcarboxamide, N-[4'-(trifluoromethylthio)-biphenyl-2-yl]-3-difluoromethyl-1-methyl-1H-pyrazol-4-ylcarboxamide, 3-(difluoromethyl)-1-methyl-N-[1,2,3,4-tetrahydro-9-(1-methylethyl)-1,4-methanonaphthalen-5-yl]-1H-pyrazol-4-ylcarboxamide, N-(3'-chloro-5-fluorobiphenyl-2-yl)-3-(difluoromethyl)-1-methylpyrazol-4-ylcarboxamide, N-(4'-chloro-5-fluorobiphenyl-2-yl)-3-(difluoromethyl)-1-methylpyrazol-4-ylcarboxamide, N-(4'-chlorobiphenyl-2-yl)-3-(difluoromethyl)-1-methylpyrazol-4-ylcarboxamide, N-(4'-bromobiphenyl-2-yl)-3-(difluoromethyl)-1-methylpyrazol-4-ylcarboxamide, N-(4'-iodobiphenyl-2-yl)-3-(difluoromethyl)-1-methylpyrazol-4-ylcarboxamide, N-(3',5'-difluorobiphenyl-2-yl)-3-(difluoromethyl)-1-methylpyrazol-4-ylcarboxamide, N-(2-chloro-4-fluorophenyl)-3-(difluoromethyl)-1-methylpyrazol-4-ylcarboxamide, N-(2-bromo-4-fluorophenyl)-3-(difluoromethyl)-1-methylpyrazol-4-ylcarboxamide and N-(2-iodo-4-fluorophenyl)-3-(difluoromethyl)-1-methylpyrazol-4-ylcarboxamide.

The preparation of difluoromethyl-substituted pyrazole derivatives will be illustrated hereinafter with reference to examples.

EXAMPLE 1

Preparation of 3-difluoromethyl-1,4-dimethylpyrazole from 1,1,2,2-tetrafluoroethyldimethylamine and ethyl prop-1-enyl ether To a solution of 1,1,2,2-tetrafluoroethyldimethylamine (3.2 g, 22 mmol) in diethyl ether (10 ml) and dioxane (10 ml) was added dropwise, under a nitrogen atmosphere, at a temperature of from 0 to 5° C., a solution of $BF_3$-etherate (49% $BF_3$, 5.6 ml, 44 mmol). After the addition had ended, the reaction mixture was stirred for 5 min. Subsequently, pyridine (1.7 g, 22 mmol) and a solution of ethyl prop-1-enyl ether (1.7 g, 20 mmol) in dioxane (2 ml) were added dropwise successively to the reaction mixture at a temperature of from 0 to 5° C. After stirring at room temperature for 6 hours, the reaction mixture was added at a temperature of from 0 to 5° C. to a mixture of sodium hydroxide (4.4 g, 110 mmol) and methylhydrazine (1.4 g, 30 mmol) in water (75 ml) and then stirred at room temperature for 3 h. Subsequently, water (50 ml) was added and the mixture was extracted with methyl tert-butyl ether. The resulting organic phases were dried over sodium sulfate, filtered and freed from the solvent under reduced pressure. 3-Difluoromethyl-1,4-dimethylpyrazole was obtained in a yield of 25%.

EXAMPLE 2

Preparation of 3-difluoromethyl-1-methylpyrazole-4-carboxylic acid from 1,1,2,2-tetrafluoroethyldimethylamine and ethyl 3-ethoxyacrylate To a solution of 1,1,2,2-tetrafluoroethyldimethylamine (3.2 g, 22 mmol) in diethyl ether (10 ml) and dioxane (10 ml) was added dropwise, under a nitrogen atmosphere, at a temperature of from 0 to 5° C., a solution of $BF_3$-etherate (49% $BF_3$, 5.6 ml, 44 mmol). After the addition had ended, the reaction mixture was stirred for 5 min. Subsequently, pyridine (1.7 g, 22 mmol) and a solution of ethyl 3-ethoxyacrylate (2.9 g, 20 mmol) in dioxane (2 ml) were added dropwise successively to the reaction mixture at a temperature of from 0 to 5° C. After stirring at room temperature for 6 hours, the reaction mixture was added at a temperature of from 0 to 5° C. to a mixture of sodium hydroxide (4.4 g, 110 mmol) and methylhydrazine (1.4 g, 30 mmol) in water (75 ml) and then stirred at room temperature for 1 h. Subsequently, the reaction mixture was heated to 60° C. and stirred at this temperature for 0.5 h. The reaction mixture was freed of volatile constituents. The resulting residue was taken up in water (50 ml), washed with ethyl acetate and then brought to a pH of 2 with conc. hydrochloric acid. The precipitated solid was isolated by filtration, washed with water and dried under reduced pressure at a temperature of 50° C. Isomerically pure 3-difluoromethyl-1-methylpyrazole-4-carboxylic acid was obtained in a yield of 50%.

EXAMPLE 3

Preparation of 3-difluoromethyl-1-methylpyrazole-4-carboxylic acid from 1,1,2,2-tetrafluoroethyldimethylamine and methyl 3-methoxyacrylate To a solution of 1,1,2,2-tetrafluoroethyldimethylamine (30 g, 207 mmol) in diethyl ether (90 ml) and dioxane (90 ml) was added dropwise, under a nitrogen atmosphere, at a temperature of from 0 to 5° C., a solution of $BF_3$-etherate (49% $BF_3$, 59.6 ml, 420 mmol). After the addition had ended, the reaction mixture was stirred for 5 min. Subsequently, pyridine (15.9 g, 201 mmol) and methyl 3-methoxyacrylate (22.3 g, 186 mmol) were successively added dropwise to the reaction mixture at a temperature of from 0 to 5° C. After stirring for 6 hours, a greasy solid formed, from which the supernatant solution was decanted off and discarded. The solid was then added at a temperature of from 0 to 5° C. to a mixture of sodium hydroxide (41.4 g, 1.035 mol) and methylhydrazine (38.6 g of a 35% aqueous solution, 288 mmol) in water (665 ml) and then stirred at room temperature for 1 h. Subsequently, the reaction mixture was heated to 60° C. and stirred at this temperature for 0.5 h. The reaction mixture was freed of volatile constituents. The resulting residue was taken up in water (50 ml), washed with ethyl acetate and then brought to a pH of 2 with conc. hydrochloric acid. The solid precipitated at a temperature of 0° C. was isolated by filtration, washed with a little ice-cold water and dried under reduced pressure at a temperature of 40° C. 3-Difluoromethyl-1-methylpyrazole-4-carboxylic acid was obtained as a mixture with 5-difluoromethyl-1-methylpyrazole-4-carboxylic acid with a ratio of 85:15 in an amount of 10.1 g.

EXAMPLE 4

Preparation of 3-difluoromethyl-1-methylpyrazole-4-carboxylic acid from 1,1,2,2-tetrafluoroethyldimethylamine and ethyl 3-pyrrolidin-1-ylacrylate To a solution of 1,1,2,2-tetrafluoroethyldimethylamine (3.2 g, 22 mmol) in diethyl ether (10 ml) and dioxane (10 ml) was added dropwise, under a nitrogen atmosphere, at a temperature of from 0 to 5° C., a solution of $BF_3$-etherate (49% $BF_3$, 5.6 ml, 44 mmol). After the addition had ended, the reaction mixture was stirred for 5 min. Subsequently, pyridine (1.7 g, 22 mmol) and a solution of ethyl 3-(pyrrolidin-1-yl)acrylate (2.9 g, 20 mmol) in dioxane (2 ml) were successively added dropwise to the reaction mixture at a temperature of from 0 to 5° C. After stirring for 6 hours, the reaction mixture was added at a temperature of from 0 to 5° C. to a mixture of sodium hydroxide (4.4 g, 110 mmol) and methylhydrazine (1.4 g, 30 mmol) in water (75 ml), and then the mixture was stirred at room temperature for 3 h. The reaction mixture was freed of volatile constituents. The resulting residue was taken up in water (50 ml), washed with ethyl acetate and then brought to a pH of 2 with conc. hydrochloric acid. The aqueous phase was decanted off and discarded. The resulting slimy residue was taken up in a mixture of tetrahydrofuran and methyl tert-butyl ether, dried over sodium sulfate, filtered and freed from the solvent under reduced pressure. 3-Difluoromethyl-1-methylpyrazole-4-carboxylic acid was obtained as a mixture with 5-difluoromethyl-1-methylpyrazole-4-carboxylic acid with a ratio of 2:1 in a yield of 60%.

EXAMPLE 5

Preparation of methyl 3-difluoromethyl-1-methylpyrazole-4-carboxylate from 1,1,2,2-tetrafluoroethyldimethylamine and methyl 3-methoxyacrylate To a solution of 1,1,2,2-tetrafluoroethyldimethylamine (96%, 46 g, 305 mmol) in acetonitrile (100 ml) was added dropwise, at 25° C. under Argon, $BF_3$-etherate (38.9 g, 274 mmol). Subsequently, under reflux conditions (approx. 70° C.), a solution of methyl 3-methoxyacrylate (95%, 33.5 g, 274 mmol) in acetonitrile (75 ml) was added dropwise to the reaction mixture within 1 h. After stirring under reflux conditions for 21 h, the reaction mixture was cooled to 25° C. The resulting reaction mixture was added dropwise to a solution of methylhydrazine (21 g, 457 mmol) in acetonitrile (48 ml) at 0 to 15° C. within 1.5 h. After stirring at 25° C. for 0.5 h, water (100 ml) was added. The reaction mixture was extracted once with 150 ml and once with 90 ml of methylene chloride. The combined organic phases were washed with water (1×200 ml). The resulting organic phase (530 g) contained, according to GC area % analysis, methyl 3-difluoromethyl-1-methylpyrazole-4-carboxylate and methyl 5-difluoromethyl-1-methylpyrazole-4-carboxylate in a ratio of 6.8:1. According to quantitative HPLC analysis, the organic phase comprised 6.7% by weight of methyl 3-difluoromethyl-1-methylpyrazole-4-carboxylate. This corresponds to a yield of 68% (based on methyl 3-methoxyacrylate).

EXAMPLE 6

Preparation of 3-difluoromethyl-1-methylpyrazole-4-carboxylic acid from 1,1,2,2-tetrafluoroethyldimethylamine and methyl 3-methoxyacrylate Step A): To a solution of 1,1,2,2-tetrafluoroethyldimethylamine (96%, 48.1 g, 318 mmol) in acetonitrile (97 g) were added dropwise, at 25° C. under argon, $BF_3$-etherate (38.4 g, 270 mmol). Subsequently, under reflux conditions (approx. 70° C.), a solution of methyl 3-methoxyacrylate (95%, 33.1 g, 271 mmol) in acetonitrile (61 g) was added dropwise to the reaction mixture within 1 h. After stirring under reflux conditions for 17.5 h, the reaction mixture was cooled to 25° C.

To monitor the course of the reaction, samples of the reaction mixture were taken during this reaction and analyzed by means of NMR spectroscopy. The cation of the compound of the formula II.b.6 (or the Lewis adduct thereof)

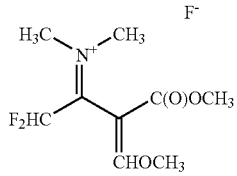

(II.b.6)

was detected in the reaction mixture on the basis of the following NMR shifts:

$^1$H NMR (500 MHz, acetonitrile): δ=7.8 (s, 1H), 6.7 (t, 1H; $^1J_{HF}$ 50 Hz), 3.96 (s, 3H), 3.63 (s, 3H,), 3.55 (s, 3H), 3.47 ppm (s, 3H); $^{13}$C NMR (125 MHz, acetonitrile): δ=47, 50, 53, 100, 110, 164, 172 (=CH—OCH$_3$), 172 ppm (—C=N$^+$(CH$_3$)$_2$); $^{15}$N NMR (500 MHz, acetonitrile, ext. standard: CH$_3$NO$_2$): −167 ppm.

Step B): Alternative 1 (with aqueous methylhydrazine)

Half of the reaction mixture obtained in step A) was added dropwise at 0 to 15° C. to an aqueous methylhydrazine solution (30%, 38.2 g, 249 mmol) within 0.5 h. After stirring at 25° C. for a further 0.5 h, a solution of NaOH in methanol (12.9% by weight, 148.3 g, 478 mmol) was added to the reaction mixture at 25 to 30° C. The reaction mixture was stirred at 25° C. for a further 12 h. Subsequently, the reaction mixture was freed of volatile constituents under reduced pressure. The residue was taken up in water (130 ml) and washed with toluene (50 ml). Thereafter, the pH was adjusted to pH 1 with hydrochloric acid (conc., 111 g). The yellowish solid which precipitates out was filtered off, washed with water (25 ml) and dried at 25° C. under reduced pressure. 3-Difluoromethyl-1-methylpyrazole-4-carboxylic acid was obtained as a solid (yield: 12.6 g; purity according to HPLC: 92 area % or 70% by weight).

Step B): Alternative 2 (with anhydrous methylhydrazine)

The second half of the reaction mixture obtained in step A) was added dropwise at 0 to 15° C. to a solution of methylhydrazine in acetonitrile (30%, 36.6 g, 239 mmol) within 0.5 h. After stirring at 25° C. for a further 0.5 h, a solution of NaOH in methanol (12.9% by weight, 148.3 g, 478 mmol) was added to the reaction mixture at 25 to 30° C. The reaction mixture was stirred at 25° C. for a further 12 h. Subsequently, the reaction mixture was freed of volatile constituents under reduced pressure. The residue was taken up in water (130 ml) and washed with toluene (50 ml). Thereafter, the pH was adjusted to pH 1 with hydrochloric acid (conc., 110 g). The yellowish solid which precipitates out was filtered off, washed with water (25 ml) and dried at 25° C. under reduced pressure. 3-Difluoromethyl-1-methylpyrazole-4-carboxylic acid was obtained as a solid (yield: 13.1 g; purity according to HPLC: 92 area % or 70% by weight).

EXAMPLE 7

Preparation of methyl 3-difluoromethyl-1H-pyrazole-4-carboxylate from 1,1,2,2-tetrafluoroethyldimethylamine and methyl 3-methoxyacrylate To a solution of 1,1,2,2-tetrafluoroethyldimethylamine (96%, 46 g, 305 mmol) in acetonitrile (100 ml) was added dropwise, at 25° C. under argon, $BF_3$-etherate (36.8 g, 259 mmol). Subsequently, under reflux conditions (approx. 70° C.), a solution of methyl 3-methoxyacrylate (95%, 31.6 g, 259 mmol) in acetonitrile (75 ml) was added dropwise to the reaction mixture within 1 h. After stirring under reflux conditions for a further 26 h, the reaction mixture was cooled to 25° C. The resulting reaction mixture was added dropwise at 0 to 15° C. to a solution of hydrazine hydrate (66.5 g, 850 mmol) in acetonitrile (100 ml) within 1 h. After stirring at 25° C. for a further hour, a sample of the solution was taken and analyzed by HPLC analysis. According to HPLC analysis, the reaction mixture comprised, as the main product (53 area %) methyl 3-difluoromethyl-1H-pyrazole-4-carboxylate (retention time: 10 min; HPLC-MS: (m/z)=177).

The invention claimed is:
1. A process for preparing compounds of the formula (I)

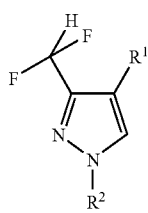

in which
$R^1$ is hydrogen, halogen, nitro, $C_1$-$C_8$-alkyl, $C_1$-$C_8$-haloalkyl, $C_3$-$C_8$-cycloalkyl, phenyl, naphthyl, hetaryl, cyano, —C(=O)—$OR^{1a}$, —C(=O)—$NR^{1b}R^{1c}$, —C(=O)—$SR^{1d}$ or —C(=S)—$SR^{1e}$, where the phenyl, naphthyl and hetaryl groups are each unsubstituted or have 1, 2 or 3 substituents selected independently from the group consisting of halogen, CN, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio, —C(=O)—$OR^{1f}$, —C(=O)—$NR^{1g}R^{1h}$, S(=O)—$R^{1i}$ and S(=O)$_2$—$R^{1j}$, where
$R^{1a}$, $R^{1d}$, $R^{1e}$, $R^{1f}$ are each independently $C_1$-$C_8$-alkyl, $C_1$-$C_8$-haloalkyl, $C_3$-$C_8$-cycloalkyl, $C_1$-$C_4$-alkoxy-$C_1$-$C_4$-alkyl, $C_3$-$C_8$-cycloalkoxy -$C_1$-$C_4$-alkyl, $C_2$-$C_8$-alkenyl, benzyl or phenyl, where the phenyl group in benzyl and phenyl is in each case unsubstituted or has 1, 2 or 3 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy, $R^{1b}$ is hydrogen, $C_1$-$C_8$-alkyl, $C_1$-$C_8$-haloalkyl, $C_3$-$C_8$-cycloalkyl, benzyl, phenyl or biphenylyl, where the phenyl groups in benzyl, phenyl and biphenylyl are each unsubstituted or have 1, 2 or 3 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy, where phenyl may have, as substituents, additional $C_3$-$C_8$-cycloalkyl which is unsubstituted or has at least one substituent selected from the group consisting of halogen and $C_3$-$C_8$-cycloalkyl, $R^{1c}$, $R^{1g}$ and $R^{1h}$ are each independently hydrogen, $C_1$-$C_8$-alkyl, $C_1$-$C_8$-haloalkyl, $C_3$-$C_8$-cycloalkyl, $C_1$-$C_4$-alkoxy-$C_1$-$C_4$-alkyl, $C_3$-$C_8$-cycloalkoxy -$C_1$-$C_4$-alkyl, $C_2$-$C_8$-alkenyl, benzyl or phenyl, where the phenyl group in benzyl and phenyl is in each case unsubstituted or has 1, 2 or 3 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy, and $R^{1i}$, $R^{1j}$ are each $C_1$-$C_8$-alkyl, $C_1$-$C_8$-haloalkyl, $C_1$-$C_8$-alkoxy or $C_1$-$C_8$-haloalkoxy; and $R^2$ is methyl;

comprising

A) reacting a compound of the formula (III)

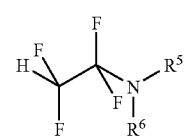

in which
$R^5$ and $R^6$ are each independently $C_1$-$C_8$-alkyl, $C_1$-$C_8$-haloalkyl, $C_3$-$C_8$-cycloalkyl, benzyl or phenyl, where the phenyl group in benzyl and phenyl is in each case unsubstituted or has 1, 2 or 3 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy, or $R^5$ and $R^6$, together with the nitrogen atom to which they are bonded, are an N-bonded 3- to 8-membered heterocycle which, as well as the nitrogen atom, may also have 1 or 2 further heteroatoms selected from the group consisting of N, O and S as ring atoms and is unsubstituted or has 1, 2, 3 or 4 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;

with an acid and a compound of the formula (IV)

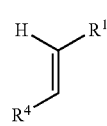

in which

R$^1$ is as defined above and

R$^4$ is halogen, —OR$^{4a}$, —SR$^{4a}$, —O—SO$_2$R$^{4a}$ or an —NR$^{4b}$R$^{4c}$ group, in which R$^{4a}$, R$^{4b}$ and R$^{4c}$ are each independently hydrogen, C$_1$-C$_8$-alkyl, C$_1$-C$_8$-haloalkyl, C$_2$-C$_8$-alkenyl, C$_3$-C$_8$-cycloalkyl, benzyl or phenyl, where the phenyl group in benzyl and phenyl is in each case unsubstituted or has 1, 2 or 3 substituents selected independently from the group consisting of halogen, CN, nitro, C$_1$-C$_4$-haloalkyl, C$_1$-C$_4$-alkoxy and C$_1$-C$_4$-haloalkoxy, or R$^{4b}$ and R$^{4c}$, together with the nitrogen atom to which they are bonded, are an N-bonded 3- to 8-membered heterocycle which, as well as the nitrogen atom, may also have 1 or 2 further heteroatoms selected from the group consisting of N, O and S as ring atoms and is unsubstituted or has 1, 2, 3 or 4 substituents selected independently from the group consisting of halogen, CN, nitro, C$_1$-C$_4$-alkyl, C$_1$-C$_4$-haloalkyl, C$_1$-C$_4$-alkoxy and C$_1$-C$_4$-haloalkoxy to obtain a reaction product (II), and B) reacting the reaction product (II) with a hydrazine compound of the formula H$_2$N —NHR$^2$ in which R$^2$ has one of the definitions given above to obtain a compound of the formula (I).

2. The process according to claim 1, wherein the reaction product (II) prepared in step A is reacted without preceding isolation with the hydrazine compound of the formula H$_2$N—NHR$^2$ to prepare compounds of the formula (I).

3. The process according to claim 1, wherein the acid used for the reaction of the compound of the formula (III) is a Lewis acid.

4. The process according to claim 1, in which R$^4$ is an —OR$^{4a}$, —SR$^{4a}$ or —NR$^{4b}$R$^{4c}$ group.

5. The process according to claim 1, in which R$^4$ is halogen, —OR$^{4a}$, —SR$^{4a}$ or —O—SO$_2$—R$^{4a}$.

6. The process according to claim 5, in which R$^4$ is —OR$^{4a}$.

7. The process according to claim 1, in which R$^5$ and R$^6$ are each independently C$_1$-C$_8$-alkyl, C$_3$C$_8$-cycloalkyl or phenyl or, together with the nitrogen atom to which they are bonded, are an N-bonded 5- or 6-membered heterocycle.

8. A process for preparing compounds of the formula (VI)

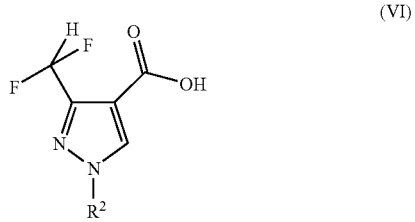
(VI)

in which

R$^2$ is methyl;

comprising i) preparing a compound of the formula (I.a) by the process of claim 1,

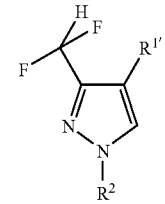
(I.a)

in which

R$^{1'}$ is CN, —C(=O)—OR$^{1aa}$, —C(=O)—NR$^{1bb}$R$^{1cc}$, —C(=O)—SR$^{1dd}$ or —C(=S)—SR$^{1ee}$, where R$^{1aa}$, R$^{1dd}$ and R$^{1ee}$ are each C$_1$-C$_8$-alkyl, C$_1$-C$_8$-haloalkyl, C$_3$-C$_8$-cycloalkyl, C$_1$-C$_4$-alkoxy-C$_1$-C$_4$-alkyl, C$_3$-C$_8$-cycloalkoxy -C$_1$-C$_4$-alkyl, C$_2$-C$_8$-alkenyl, benzyl or phenyl, R$^{1bb}$ and R$^{1cc}$ are each independently hydrogen, C$_1$-C$_8$-alkyl, C$_1$-C$_8$-haloalkyl or C$_3$-C$_8$-cycloalkyl, benzyl or phenyl, and where the phenyl group in benzyl and phenyl is in each case unsubstituted or has 1, 2 or 3 substituents each independently selected from the group consisting of halogen, CN, nitro, C$_1$-C$_4$-alkyl, C$_1$-C$_4$-haloalkyl, C$_1$-C$_4$-alkoxy and C$_1$-C$_4$-haloalkoxy, and ii) hydrolyzing the compound of the formula (I.a) to obtain a compound of the formula (VI).

9. The process according to claim 8, in which the compound of the formula (I.a) prepared in step i) is used without preceding isolation in step ii) of the process according to the invention to prepare a compound of the formula (VI).

10. A compound of the formula (II.a) or (II.b),

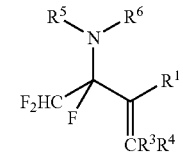
(II.a)

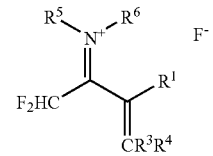
(II.b)

in which

R$^1$ is hydrogen, halogen, nitro, C$_1$-C$_8$-alkyl, C$_1$-C$_8$-haloalkyl, C$_3$-C$_8$-cycloalkyl, phenyl, naphthyl, hetaryl, cyano, —C(=O)—OR$^{1a}$, —C(=O)—NR$^{1b}$R$^{1c}$, —C(=O)—SR$^{1d}$ or —C(=S)—SR$^{1e}$, where the phenyl, naphthyl and hetaryl groups are each unsubstituted or have 1, 2 or 3 substituents selected independently from the group consisting of halogen, CN, nitro, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, C$_1$-C$_4$-haloalkylthio, —C(=O)—OR$^{1f}$, —C(=O)—NR$^{1g}$R$^{1h}$, S(=O)—R$^{1i}$ and S(=O)$_2$—R$^{1j}$, where R$^{1a}$, R$^{1d}$, R$^{1e}$, R$^{1f}$ are each independently C$_1$-C$_8$-alkyl, C$_1$-C$_8$-haloalkyl, C$_3$-C$_8$-cycloalkyl, C$_1$-C$_4$-alkoxy-C$_1$-C$_4$-alkyl, C$_3$-C$_8$-cycloalkoxy -C$_1$-C$_4$-alkyl, C$_2$-C$_8$-alkenyl, benzyl or phenyl, where the phenyl group in benzyl and phenyl is in each case unsubstituted or has 1, 2 or 3 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy, $R^{1b}$ is hydrogen, $C_1$-$C_8$-alkyl, $C_1$-$C_8$-haloalkyl, $C_3$-$C_8$-cycloalkyl, benzyl, phenyl or biphenylyl, where the phenyl groups in benzyl, phenyl and biphenylyl are each unsubstituted or have 1, 2 or 3 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy, where phenyl may have, as substituents, additional $C_3$-$C_8$-cycloalkyl which is unsubstituted or has at least one substituent selected from the group consisting of halogen and $C_3$-$C_8$-cycloalkyl, $R^{1c}$, $R^{1g}$ and $R^{1h}$ are each independently hydrogen, $C_1$-$C_8$-alkyl, $C_1$-$C_8$-haloalkyl, $C_3$-$C_8$-cycloalkyl, $C_1$-$C_4$-alkoxy-$C_1$-$C_4$-alkyl, $C_3$-$C_8$-cycloalkoxy-$C_1$-$C_4$-alkyl, $C_2$-$C_8$-alkenyl, benzyl or phenyl, where the phenyl group in benzyl and phenyl is in each case unsubstituted or has 1, 2 or 3 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy, and $R^{1i}$, $R^{1j}$ are each $C_1$-$C_8$-alkyl, $C_1$-$C_8$-haloalkyl, $C_1$-$C_8$-alkoxy or $C_1$-$C_8$-haloalkoxy;

$R^3$ is hydrogen;

$R^4$ is halogen, —$OR^{4a}$, —$SR^{4a}$, —O—$SO_2$—$R^{4a}$ or an —$NR^{4b}R^{4c}$ group, in which $R^{4a}$, $R^{4b}$ and $R^{4c}$ are each independently hydrogen, $C_1$-$C_8$-alkyl, $C_1$-$C_8$-haloalkyl, $C_2$-$C_8$-alkenyl, $C_3$-$C_8$-cycloalkyl, benzyl or phenyl, where the phenyl group in benzyl and phenyl is in each case unsubstituted or has 1, 2 or 3 substituents selected independently from the group consisting of halogen, CN, nitro, $C_1$-$C_4$-haloalkyl, $C_1$-$C_4$-alkoxy and $C_1$-$C_4$-haloalkoxy, or $R^{4b}$ and $R^{4c}$, together with the nitrogen atom to which they are bonded, are an N-bonded 3- to 8-membered heterocycle which, as well as the nitrogen atom, may also have 1 or 2 further heteroatoms selected from the group consisting of N, O and S as ring atoms and is unsubstituted or has 1, 2, 3 or 4 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy $R^5$ and $R^6$ are each independently $C_1$-$C_8$-alkyl, $C_1$-$C_8$-haloalkyl, $C_3$-$C_8$-cycloalkyl, benzyl or phenyl, where the phenyl group in benzyl and phenyl is in each case unsubstituted or has 1, 2 or 3 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy, or $R^5$ and $R^6$, together with the nitrogen atom to which they are bonded, are an N-bonded 3- to 8-membered heterocycle which, as well as the nitrogen atom, may also have 1 or 2 further heteroatoms selected from the group consisting of N, O and S as ring atoms and is unsubstituted or has 1, 2, 3 or 4 substituents selected independently from the group consisting of halogen, CN, nitro, $C_1$-$C_4$-alkyl, $C_1$-$C_4$-haloalkyl, $C_1$-$C_4$-alkoxy and $C_1$-$C_4$-haloalkoxy;

or a Lewis acid adduct of a compound of the formula (II.b).

11. The compound of the formula (II.a) or (II.b) or a Lewis acid adduct of a compound of the formula (II.b) according to claim 10, in which $R^4$ is halogen, —$OR^{4a}$, —$SR^{4a}$ or —O—$SO_2$—$R^{4a}$.

12. The compound of the formula (II.a) or (II.b) or a Lewis acid adduct of a compound of the formula (II.b) according to claim 10, in which $R^4$ is —$OR^{4a}$.

* * * * *

UNITED STATES PATENT AND TRADEMARK OFFICE
CERTIFICATE OF CORRECTION

PATENT NO. : 8,188,295 B2
APPLICATION NO. : 12/664448
DATED : May 29, 2012
INVENTOR(S) : Markus Nett et al.

It is certified that error appears in the above-identified patent and that said Letters Patent is hereby corrected as shown below:

In Claim 1, col. 21, line 12, after "nitro" insert --$C_1$-$C_4$-alkyl,--.

In Claim 7, col. 21, line 46, delete "$C_3C_8$" and insert therefore --$C_3$-$C_8$--.

In Claim 10, col. 22, line 54, delete "$SR^{le}$" and insert therefore --$SR^{1e}$--; and col. 23, line 35, after "nitro," insert --$C_1$-$C_4$-alkyl,--.

Signed and Sealed this
Second Day of October, 2012

David J. Kappos
*Director of the United States Patent and Trademark Office*